United States Patent [19]

Kroenke

[11] 4,153,792

[45] May 8, 1979

[54] MELAMINE MOLYBDATE

[75] Inventor: William J. Kroenke, Brecksville, Ohio

[73] Assignee: The B. F. Goodrich Company, Akron, Ohio

[21] Appl. No.: 792,293

[22] Filed: Apr. 29, 1977

Related U.S. Application Data

[62] Division of Ser. No. 770,168, Feb. 14, 1977, Pat. No. 4,053,455.

[51] Int. Cl.$^2$ ............................................ C07D 251/70
[52] U.S. Cl. ........................... 544/181; 260/45.8 NT; 544/4; 544/64; 546/8; 260/429 R
[58] Field of Search ......................................... 544/181

[56] References Cited

U.S. PATENT DOCUMENTS 3,028,255  4/1962  Owen .................................. 117/36.8

OTHER PUBLICATIONS

Arnaud-New et al., "Photochromism of Amine Molybdates", *Chemistry and Uses of Molybdenum*, Mitchell, ED, Climax Molybdenum Co., London, (1974), pp. 35–38.

Arnaud-New et al., *Bull. de la Soc. Chim. de France*, (1973), No. 12, pp. 3225–3246.

Marzluff, *Inorganic Chemistry*, vol. 3, No. 3, (1964), pp. 395–397.

*Primary Examiner*—John M. Ford
*Attorney, Agent, or Firm*—Charles A. Crehore

[57] ABSTRACT

Amine molybdates retard smoke formation effectively when vinyl chloride and vinylidene chloride polymers burn.

5 Claims, No Drawings

MELAMINE MOLYBDATE

This is a division of application Ser. No. 770,168, filed Feb. 14, 1977, now U.S. Pat. No. 4,053,455.

BACKGROUND OF THE INVENTION

Vinyl chloride and vinylidene chloride polymers are known to be self-extinguishing and relatively more flame retardant than other polymers such as polyethylene, polypropylene and the like. However, a substantial amount of smoke may be produced upon exposure of vinyl chloride and vinylidene chloride polymers to a flame. The fact that an additive is a flame retardant does not necessarily mean that it will have good smoke retardant properties, as is well known to those skilled in the art.

U.S. Pat. Nos. 3,821,151, 3,845,001, 3,870,679 and 3,903,028 teach use of certain molybdenum compounds, alone or in combination with other compounds, as smoke retardants in PVC. The specific compounds listed therein suffer from the disadvantages that most, such as $MoO_3$, are colored compounds giving an unsatisfactory tint to compositions in which they are used. Even white or lightly colored molybdenum compounds such as the ammonium or sodium molybdates tend to discolor the PVC compositions, and also give less satisfactory smoke reduction than $MoO_3$.

New, highly effective smoke retardant vinyl chloride and vinylidene chloride polymer compositions are desired.

SUMMARY OF THE INVENTION

Amine molybdates are effective smoke retardant additives for vinyl chloride and vinylidene chloride polymers. Melamine molybdate is preferred, since it is both white and highly effective as a smoke retardant in vinyl chloride and vinylidene chloride polymers. Melamine molybdate also processes easily without discoloring the polymers.

DETAILED DESCRIPTION

Amine Molybdates

The additive amine molybdates used in this invention may be polycrystalline or amorphous fine powders, preferably with an average particle size from about 0.01 to about 800 microns, more preferably from about 0.1 to about 200 microns, and even more preferably from about 0.5 to about 50 microns. The amine molybdates are used in smoke retardant amounts, typically from about 0.01 to about 20 parts by weight, more preferably from about 1 to about 10 parts by weight, per 100 parts by weight of polymer. Supporting media such as $SiO_2$, $Al_2O_3$ and the like may be used for the smoke retardant additives and in many cases are preferred, since additive surface area is increased greatly for smoke reduction purposes.

Amine molybdates may be produced by reacting a suitable amine with a molybdenum compound such as $MoO_3$, molybdic acid or a molybdenum salt. Molybdenum salts include ammonium molybdate, ammonium dimolybdate, ammonium heptamolybdate (also called ammonium paramolybdate), ammonium octamolybdate, sodium molybdate or the like. Ammonium molybdates are preferred and include ammonium molybdate $[(NH_4)_2MoO_4]$ itself, ammonium dimolybdate $[(NH_4)_2Mo_2O_7]$, ammonium heptamolybdate $[(NH_4)_6Mo_7O_{24}.4H_2O]$, and ammonium octamolybdate $[(NH_4)_4Mo_8O_{26}.5H_2O]$. Sodium molybdate also is preferred. Excellent results were obtained using ammonium dimolybdate, ammonium heptamolybdate, sodium molybdate, and the commercial so-called "molybdic acid", which consists primarily of ammonium molybdates.

The reaction preferably is conducted in the presence of an acid in order to maximize the amine molybdate yield. Suitable acids include organic acids containing one to 12 carbon atoms such as formic acid, acetic acid, propionic acid, benzoic acid, and the like; and inorganic acids such as hydrochloric acid, nitric acid, sulfuric and the like. Mixtures of acids may also be used. Excellent results were obtained using formic acid, acetic acid, benzoic acid, hydrochloric acid, nitric acid and sulfuric acid. The amount of acid used may be varied widely from 0 to 10 equivalents and more of acid per equivalent of ammonium or other cation in a particular molybdenum salt. About a 1/1 equivalent ratio is preferred.

Suitable reaction media include water, alcohols such as ethanol or the like, and water/alcohol mixtures. Reaction components may be mixed in any order. A preferred reaction method comprises adding an aqueous solution of an ammonium molybdate or other molybdenum salt to an amine solution in dilute hydrochloric acid, followed by refluxing the reaction mixture for 0.25 to 16 hours, more preferably for 0.25 to 4 hours. Another preferred reaction method comprises charging all reaction components essentially simultaneously to a reaction vessel, followed by refluxing as just described.

The reaction mixture is stirred continuously as a slurry. When the desired reaction time has passed, the mixture is cooled to about room temperature (25° C.). The amine molybdate may be separated by filtration, centrifugation or the like and optionally washed with water, ethanol or a mixture thereof. The amine molybdate may be air dried at about 100°–200° C., or it may be vacuum dried at temperatures up to 150° C. and higher. The amine molybdate is identifiable by means of infrared and x-ray diffraction spectroscopy.

Amines suitable for preparing the amine molybdates used in this invention include polymeric amines, as well as simple amines. The simple amines may contain from 1 to 40 carbon atoms and from 1 to 10 primary, secondary, or tertiary amine groups or a mixture thereof, more preferably from 1 to 6 of such groups. Simple amines include aliphatic, alicyclic, aromatic and heterocyclic amines. Examples of suitable polymeric amines include polyethyleneimine, polyvinylpyridine, polyvinylpyrrolidine, and poly(2,2,4-trimethyl-1,2-dihydroquinolyl).

Examples of suitable simple amines include aliphatic amines such as ethylamine, ethylenediamine, 1,2-propanediamine, 1,3-propanediamine, 1,4-butanediamine, 2-methyl-1,2-propanediamine, 1,5-pentanediamine, 1,6-hexanediamine, 1,7-heptanediamine, 1,8-octanediamine, 1,10-decanediamine, 1,12-dodecanediamine and the like. Also suitable are aliphatic amines such as diethylenetriamine, triethylenetetramine, tetraethylenepentamine, bis(hexamethylene)triamine, 3,3'-iminobispropylamine, guanidine carbonate, and the like. Other suitable amines include alicyclic diamines and polyamines such as 1,2-diaminocyclohexane, 1,8-p-menthanediamine and the like; and aromatic amines such as aniline, N,N-dimethylaniline, and the like. Heterocyclic amines may also be used including melamine and substituted melamines; pyridine; piperazine; hexamethylenetetramine; 2,2,4-trimethyl decahydroquinoline; and N-

(aminoalkyl)piperazines wherein each alkyl group contains from 1 to 12 carbon atoms, more preferably 1 to 6 carbon atoms, such as N-(2-aminoethyl)-piperazine and the like.

Melamine and substituted melamines have the formula

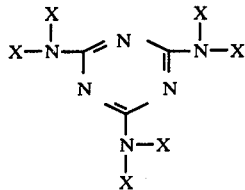

wherein X is hydrogen or an alkyl, alicyclic, aralkyl, alkaryl, aryl or heterocyclic group containing from 1 to 10 atoms of C, O, S and/or N. Two X's on each of one or more nitrogen atoms may also be joined together to form a heterocyclic ring such as a morpholino group, for example as in 2,4,6-tri(morpholino)-1,3,5-triazine. Other examples of suitable substituted melamines include N,N',N"-hexaethylmelamine; 2-anilino-4-(2',4'-dimethylanilino)-6-piperidino-1,3,5-triazine; and 2,4,6-tri(N-methylanilino)-1,3,5-triazine.

Excellent results were obtained using ethylamine; ethylenediamine; guanidine carbonate; aniline; N,N-dimethylaniline; melamine; pyridine; piperazine; hexamethylenetetramine; N,N',N"-hexaethylmelamine; 2-anilino-4-(2',4'-dimethylanilino)-6-piperidino-1,3,5-triazine; 2,4,6-tri(N-methylanilino)-1,3,5-triazine; and 2,4,6-tri(morpholino)-1,3,5-triazine. Melamine is preferred since melamine molybdate is both white and highly effective as a smoke retardant. Melamine molybdate also processes easily without discoloring the polymers.

POLYMERS AND SMOKE RETARDANT COMPOSITIONS

Vinyl chloride and vinylidene chloride polymers used in this invention include homopolymers, copolymers and blends of homopolymers and/or copolymers. The vinyl chloride and vinylidene chloride polymers may contain from 0 to about 50% by weight of at least one other olefinically unsaturated monomer, more preferably from 0 to about 50% by weight of at least one other vinylidene monomer (i.e., a monomer containing at least one terminal $CH_2=C<$ group per molecule) copolymerized therewith, even more preferably from 0 to about 20% by weight of such vinylidene monomer. Suitable monomers include 1-olefins containing from 2 to 12 carbon atoms, more preferably from 2 to 8 carbon atoms, such as ethylene, propylene, 1-butene, isobutylene, 1-hexene, 4-methyl-1-pentene, and the like; dienes containing from 4 to 10 carbon atoms including conjugated dienes as butadiene, isoprene, piperylene, and the like; ethylidene norbornene and dicyclopentadiene; vinyl esters and allyl esters such as vinyl acetate, vinyl chloroacetate, vinyl propionate, vinyl laurate, allyl acetate, and the like; vinyl aromatics such as styrene, α-methyl styrene, chlorostyrene, vinyl toluene, vinyl naphthalene, and the like; vinyl and allyl ethers and ketones such as vinyl methyl ether, allyl methyl ether, vinyl isobutyl ether, vinyl n-butyl ether, vinyl chloroethyl ether, methyl vinyl ketone, and the like; vinyl nitriles such as acrylonitrile, methacrylonitrile, and the like; cyanoalkyl acrylates such as α-cyanomethyl acrylate, the α-, β- and γ-cyanopropyl acrylates, and the like; olefinically unsaturated carboxylic acids and esters thereof, including α,β-olefinically unsaturated acids and esters thereof such as methyl acrylate, ethyl acrylate, chloropropyl acrylate, butyl acrylate, hexyl acrylate, 2-ethylhexyl acrylate, dodecyl acrylate, octadecyl acrylate, cyclohexyl acrylate, phenyl acrylate, glycidyl acrylate, methoxyethyl acrylate, ethoxyethyl acrylate, hexylthioethyl acrylate, methyl methacrylate, ethyl methacrylate, butyl methacrylate, glycidyl methacrylate, and the like, and including esters of maleic and fumaric acid, and the like; amides of the α,β-olefinically unsaturated carboxylic acids such as acrylamide, and the like; divinyls, diacrylates and other polyfunctional monomers such as divinyl benzene, divinyl ether, diethylene glycol diacrylate, ethylene glycol dimethacrylate, methylene-bis-acrylamide, allyl pentaerythritol, and the like; and bis(β-haloalkyl)alkenyl phosphonates such as bis(β-chloroethyl)vinyl phosphonate, and the like.

More preferred monomers include 1-olefins containing from 2 to 12 carbon atoms, more preferably from 2 to 8 carbon atoms, such as ethylene, propylene, 1-butene, isobutylene, 1-hexene, 4-methyl-1-pentene, and the like; vinyl esters and allyl esters such as vinyl acetate, vinyl chloroacetate, vinyl propionate, vinyl laurate, allyl acetate, and the like; olefinically unsaturated carboxylic acids and esters thereof, including α,β-olefinically unsaturated acids and esters thereof such as methyl acrylate, ethyl acrylate, chloropropyl acrylate, butyl acrylate, hexyl acrylate, 2-ethylhexyl acrylate, dodecyl acrylate, octadecyl acrylate, cyclohexyl acrylate, phenyl acrylate, glycidyl acrylate, methoxyethyl acrylate, ethoxyethyl acrylate, hexylthioacrylate, methyl methacrylate, ethyl methacrylate, butyl methacrylate, glycidyl methacrylate, and the like, and including esters of maleic and fumaric acid, and the like; and amides of α,β-olefinically unsaturated carboxylic acids such as acrylamide, and the like.

The vinyl chloride and vinylidene chloride polymers may be prepared by any method known to the art such as by emulsion, suspension, bulk or solution polymerization. The additive compounds may be mixed with the polymer emulsion, suspension, solution or bulk mass before monomer recovery and/or drying. More preferably, the compounds may be mixed with dry granular or powdered polymers. The polymers and compounds may be mixed thoroughly in granular or powder form in apparatus such as a Henschel mixer, or the like. Alternatively, this step may be eliminated and the mixing done while the polymer mass is fluxed, fused and masticated to homogeneity under fairly intensive shear in or on a mixer apparatus having its metal surface in contact with the material. The fusion temperature and time will vary according to the polymer composition and level of additive compounds but will generally be in the range of about 300° to 400° F. and 2 to 10 minutes.

Smoke retardancy may be measured using an NBS Smoke Chamber according to procedures described by Gross et al, "Method for Measuring Smoke from Burning Materials", *Symposium on Fire Test Methods—Restraint & Smoke* 1966, ASTM STP 422, pp. 166-204. Maximum smoke density ($D_m$) is a dimensionless number and has the advantage of representing a smoke density independent of chamber volume, specimen size or photometer path length, provided a consistent dimensional system is used. Percent smoke reduction is calculated using this equation:

$$\frac{D_m/g \text{ of sample} - D_m/g \text{ of control}}{D_m/g \text{ of control}} \times 100.$$

The term "$D_m/g$" means maximum smoke density per gram of sample. $D_m$ and other aspects of the physical optics of light transmission through smoke are discussed fully in the above ASTM publication.

Smoke retardance may be measured quickly using the Goodrich Smoke-Char Test. Test samples may be prepared by dry blending polymer resin and smoke retardant additives. The blend is ground in a liquid $N_2$-cooled grinder to assure uniform dispersion of the smoke retardant additives in the resin. Small (about 0.3 g) samples of the polymer blend are pressed into pellets about ¼ inch in diameter for testing. Alternatively, test samples may be prepared by blending resin, smoke retardant additives and lubricant(s) or processing aid(s) in a blender such as an Osterizer blender. The blend is milled, pressed into sheets, and cut into small (about 0.3 gram) samples for testing. The test samples are placed on a screen and burned for 60 seconds with a propane gas flame rising vertically from beneath the samples. Sample geometry at a constant weight has been found not to be significant for the small samples used in this test. A Bernz-O-Matic pencil flame burner head is used with gas pressure maintained at about 40 psig. Each sample is immersed totally and continuously in the flame. Smoke from the burning sample rises in a vertical chimney and passes through the light beam of a Model 407 Precision Wideband Photometer (Grace Electronics, Inc., Cleveland, Ohio) coupled with a photometer integrator. Smoke generation is measured as integrated area per gram of sample.

The vinyl chloride and vinylidene chloride polymer compositions of this invention may contain the usual compounding ingredients known to the art such as fillers, stabilizers, opacifiers, lubricants, processing aids, impact modifying resins, plasticizers, antioxidants, and the like.

The following examples illustrate the present invention more fully.

EXAMPLE 1

Synthesis of Melamine Molybdate in Aqueous Medium

Melamine molybdate having a 1/1 molybdenum/melamine molar ratio was prepared in a non-acid reaction medium as follows. 100 grams of melamine was dissolved in 2.5 liters of distilled water by heating to reflux in a 3-liter round-bottomed flask equipped with a water-cooled condenser. 275.30 grams of ammonium heptamolybdate was dissolved in 1-liter of hot distilled water and then added to the first solution. A white precipitate formed immediately.

The reaction mixture was refluxed for 4 hours and thereafter filtered hot through Whatman No. 42 filter paper that was backed by a Macherey, Negel and Company (Duren, Germany) MN-85 filter paper supported on a Buchner funnel. A white solid was separated and washed with three 50 ml water portions and three 50 ml ethanol portions. The solid was dried for about 16 hours at 57° C. and found to weigh 235.01 grams.

A white crystalline solid precipitated from the filtrate after it stood overnight at room temperature. The precipitate was recovered and washed as just described. It was vacuum dried for 1 hour at 70° C. and found to weigh 10.70 grams. Infrared and x-ray diffraction spectroscopic analyses demonstrated that both solids were identical, i.e., both were melamine molybdate. Total product yield was 245.71 grams.

EXAMPLES 2-18

Examples 2-18 summarized in Table I illustrate the production of melamine molybdate having a 1/1 molybdenum/melamine molar ratio using the general reaction and recovery procedures of Example 1 in an aqueous medium.

TABLE I

| Example | Starting Molybdenum Compound (grams)+ | Melamine (grams) | Molybdenum/Melamine Molar Ratio in Reactants | $H_2O$ (ml) | Reaction Time | Melamine Molybdate Yield (grams) |
|---|---|---|---|---|---|---|
| 2 | 2.57 (m) | 2.00 | 0.96 | 100 | 3 min. | 1.50 |
| 3 | 5.14 (m) | 4.00 | 0.96 | 250 | 1 hr. | 5.25 |
| 4 | 13.34 (m) | 10.00 | 1.0 | 344 | 4 hr. | 7.60 |
| 5 | 10.27 (m) | 4.00 | 1.9 | 275 | 5 min. | 8.15 |
| 6 | 10.27 (m) | 4.00 | 1.9 | 275 | 5 min. | 7.72 |
| 7 | 275.30 | 100.00 | 2.0 | 3500 | 15 min. | 247.22 |
| 8 | 275.30 | 100.0 | 2.0 | 3500 | 35 min. | 245.23 |
| 9 | 10.27 (m) | 4.00 | 1.9 | 275 | 1 hr. | 8.20 |
| 10 | 275.30 | 100.00 | 2.0 | 3500 | 3 hr. | 235.01 |
| 11 | 13.88 | 5.00 | 2.0 | 344 | 4 hr. | 10.76 |
| 12 | 275.30 | 100.00 | 2.0 | 3500 | 4 hr. | 237.67 |
| 13 | 13.34 (m) | 5.00 | 2.0 | 344 | 17 hr. | 9.80 |
| 14 | 7.70 (m) | 2.00 | 2.9 | 150 | 1 min. | 4.50 |
| 15 | 15.41 (m) | 4.00 | 2.9 | 300 | 5 min. | 9.80 |
| 16 | 15.41 (m) | 4.00 | 2.9 | 300 | 1 hr. | 9.83 |
| 17 | 15.41 (m) | 4.00 | 2.9 | 300 | 4 hr. | 10.15 |
| 18 | 13.34 (m) | 3.33 | 3.0 | 344 | 4 hr. | 6.50 |

+Ammonium heptamolybdate used, except where indicated otherwise.
(m) = "Baker 0206 Molybdic Acid" which comprises primarily at least one ammonium molybdate.

EXAMPLES 19-39

Examples 19-39 summarized in Table II illustrate the production of melamine molybdate using the general reaction and recovery procedures of Example 1 in an aqueous HCl medium. The melamine molybdate produced in Examples 19-24 had a 1/1 molybdenum/melamine molar ratio. In Examples 26-39 the melamine molybdate produced had a 2/1 molybdenum/melamine molar ratio. The product in Example 25 was a mixture of the 1/1 and 2/1 molybdenum/melamine molar ratio melamine molybdates.

TABLE II

| Example | Starting Ammonium Molybdate (grams)+ | Melamine (grams) | Molybdenum/Melamine Molar Ratio in Reactants | H₂O (ml) | 37% HCl (grams) | Reaction Time | Melamine Molybdate Yield (grams) |
|---|---|---|---|---|---|---|---|
| 19 | 2.80 | 2.00 | 1.0 | 60 | 1.34 | 5 min. | 4.28 |
| 20 | 14.00 | 10.00 | 1.0 | 275 | 6.70 | 15 min. | 21.45 |
| 21 | 13.48 (D) | 10.00 | 1.0 | 275 | 7.81 | 30 min. | 21.88 |
| 22 | 13.48 (D) | 10.00 | 1.0 | 175 | 7.81 | 30 min. | 20.99 |
| 23 | 140.00 | 100.00 | 1.0 | 2750 | 67.0 | 3.3 hr. | 211.23 |
| 24 | 14.00 | 10.00 | 1.0 | 275 | 6.70 | 4 hr. | 21.80 |
| 25 | 21.00 | 10.00 | 1.5 | 288 | 10.05 | 2 hr. | 28.35 |
| 26 | 28.00 | 10.00 | 2.0 | 300 | 13.40 | 15 min. | 32.58 |
| 27 | 28.00 | 10.00 | 2.0 | 200 | 13.40 | 30 min. | 34.45 |
| 28 | 26.95 (D) | 10.00 | 2.0 | 200 | 15.62 | 30 min. | 32.79 |
| 29 | 28.00 | 10.00 | 2.0 | 200 | 13.40 | 30 min. | 33.48 |
| 30 | 28.00 | 10.00 | 2.0 | 150 | 13.40 | 30 min. | 33.48 |
| 31 | 28.00 | 10.00 | 2.0 | 300 | 13.40 | 30 min. | 33.50 |
| 32 | 280.00 | 100.00 | 2.0 | 3000 | 134.0 | 30 min. | 339.55 |
| 33 | 23.00 | 10.00 | 2.0 | 200 | 13.40 | 2 hr. | 33.02 |
| 34 | 26.95 (D) | 10.00 | 2.0 | 300 | 15.63 | 3 hr. | 32.96 |
| 35 | 28.00 | 10.00 | 2.0 | 300 | 13.40 | 4 hr. | 32.58 |
| 36 | 280.00 | 100.00 | 2.0 | 3000 | 134.0 | 4.2 hr. | 333.94 |
| 37 | 28.00 | 10.00 | 2.0 | 150 | 13.40 | 4 hr. | 32.80 |
| 38 | 28.00 | 10.00 | 2.0 | 200 | 13.40 | 16 hr. | 32.70 |
| 39 | 28.00 | 10.00 | 2.0 | 300 | 13.40 | 16 hr. | 32.68 |

+Ammonium heptamolybdate used, except where indicated otherwise (D = ammonium dimolybdate).

EXAMPLE 40

Synthesis of Melamine Molybdate in Aqueous Formic Acid Medium

Melamine molybdate was prepared in the presence of formic acid as follows. 10 grams of melamine, 7.30 grams of formic acid, and 250 ml water were dissolved together by refluxing in a 500 ml. round-bottomed flask equipped with a stirrer and water-cooled condenser. 26.95 grams of ammonium dimolybdate was dissolved in 50 ml hot water and then added to the first solution. A white precipitate formed immediately.

The reaction mixture was refluxed for one hour and filtered hot as in Example 1. A white solid was recovered and washed three times with water. The solid weighed 29.25 grams after being vacuum dried for 3.25 hours at 120° C.

EXAMPLE 41

Synthesis of Melamine Molybdate in Aqueous Acetic Acid Medium

Melamine molybdate was prepared in the presence of acetic acid as follows. 10 grams of melamine, 9.52 grams of acetic acid, and 250 ml water were dissolved together by refluxing in a 500 ml round-bottomed flask equipped with a stirrer and water-cooled condenser. 26.95 grams of ammonium dimolybdate was dissolved in 50 ml. hot water and then added to the first solution. A white precipitate formed immediately.

The reaction mixture was refluxed for one hour, cooled to room temperature (about 25° C.), and filtered through Whatman No. 42 filter paper that was backed by a Macherey, Negel and Company (Duren, Germany) MN-85 filter paper supported on a Buchner funnel. A white solid was recovered and washed three times with water. The solid weighed 28.38 grams after being vacuum dried for 3 hours at 120° C.

EXAMPLE 42

Synthesis of Melamine Molybdate in Aqueous Benzoic Acid Medium

Melamine molybdate was prepared in the presence of benzoic acid as follows. 5 grams of melamine, 9.68 grams of benzoic acid, and 250 ml water were dissolved together by refluxing in a 500 ml round-bottomed flask equipped with a stirrer and water-cooled condenser. 13.47 grams of ammonium dimolybdate was dissolved in 25 ml hot water and then added to the first solution. A white precipitate formed immediately.

The reaction mixture was refluxed for one hour and filtered hot as in Example 1. A white solid was recovered and washed three times with water. The solid weighed 13.04 grams after being vacuum dried for 3 hours at 120° C.

EXAMPLE 43

Synthesis of Ethylamine Molybdate in Aqueous HCl Medium

Ethylamine molybdate having a 1/1 molybdenum/ethylamine molar ratio was prepared in the presence of HCl as follows. 14.29 grams of a 70 wt.% ethylamine aqueous solution, 21.85 grams of a 37 wt.% aqueous HCl solution, and 150 ml water were dissolved together and heated to reflux in a 500 ml. round-bottomed flask equipped with a stirrer and water-cooled condenser. 37.70 grams of ammonium dimolybdate was dissolved in 80 ml hot water and then added to the first solution.

The reaction mixture was refluxed for 1.5 hours, cooled to room temperature (about 25° C.), and filtered as in Example 41. A white solid was recovered and washed four times with water. The solid was vacuum dried for 2 hours at 120° C. The final product was a fluffy white solid weighing 26.68 grams.

EXAMPLE 44

Synthesis of Ethylenediamine Molybdate in Aqueous HCl Medium

Ethylenediamine molybdate having a 2/1 molybdenum/ethylenediamine molar ratio was prepared in the presence of HCl as follows. 5.10 grams ethylenediamine, 16.39 grams of a 37 wt.% aqueous HCl solution, and 125 ml water were dissolved together and heated to reflux in a 500 ml. round-bottomed flask equipped with a stirrer and water-cooled condenser. 28.28 grams of ammonium dimolybdate was dissolved in 53 ml hot water and then added to the first solution.

The reaction mixture was refluxed for 1 hour, cooled to room temperature and filtered as in Example 41. A white solid was recovered and washed three times with water. The solid was vacuum dried for 2 hours at 120° C. The final product was a white solid weighing 21.39 grams. It appeared to be photochromic, changing to a pale pink color after brief exposure to light.

EXAMPLE 45

Synthesis of Guanidine Molybdate in Aqueous HCl Medium

Guanidine molybdate having a 2/1 molybdenum/-quanidine molar ratio was prepared in the presence of HCl as follows. 10 grams guanidine carbonate, 21.88 grams of 37 wt.% aqueous HCl solution, and 250 ml water were dissolved together and heated to reflux in a 500 ml round-bottomed flask equipped with a water-cooled condenser. 37.74 grams of ammonium dimolybdate was dissolved in 70 ml hot water and then added to the first solution.

The reaction mixture was refluxed for 1 hour, cooled to room temperature, and filtered as in Example 41. A yellow solid was recovered and washed three times with water. The solid was vacuum dried for 2 hours at 120° C. The final product was a pale yellow powder weighing 37.50 grams.

EXAMPLE 46

Synthesis of Aniline Molybdate in Aqueous HCl Medium

Aniline molybdate having a 2/1 molybdenum/aniline molar ratio was prepared in the presence of HCl as follows. 10 grams of aniline, 21.16 grams of a 37 wt.% aqueous HCl solution, and 250 ml water were dissolved together and heated to reflux in 500 ml round-bottomed flask equipped with a stirrer and water-cooled condenser. 36.50 grams of ammonium dimolybdate was dissolved in 68 ml hot water and then added to the first solution.

The reaction mixture was refluxed for 1 hour, cooled to room temperature, and filtered as in Example 41. A light gray solid was recovered and washed three times with water. The solid was vacuum dried for 2.5 hours at 120° C. The final product was a slightly off-white solid weighing 38.01 grams.

EXAMPLE 47

Synthesis of N,N-dimethylaniline Molybdate in Aqueous HCl Medium

N,N-dimethylaniline molybdate having a 2/1 molybdenum/N,N-dimethylaniline molar ratio was prepared in the presence of HCl as follows. 10 grams of N,N-dimethylaniline, 16.26 grams of a 37 wt.% aqueous HCl solution, and 250 ml water were dissolved together and heated to reflux in a 500 ml round-bottomed flask equipped with a water-cooled condenser. 28.05 grams of ammonium dimolybdate was dissolved in 52 ml hot water and then added to the first solution.

The reaction mixture was refluxed for 1 hour, cooled to room temperature, and filtered as in Example 41. A solid was recovered and washed three times with water. The solid was vacuum dried for 2.5 hours at 120° C. The final product was a pale bluish-white solid weighing 29.74 grams.

EXAMPLE 48

Synthesis of Pyridine Molybdate in Aqueous HCl Solution

Pyridine molybdate having a 2/1 molybdenum/pyridine molar ratio was prepared in the presence of HCl as follows. 10 grams of pyridine, 24.92 grams of a 37 wt.% aqueous HCl solution, and 150 ml water were dissolved together and heated to reflux in a 500 ml round-bottomed flask equipped with a stirrer and water-cooled condenser. 42.98 grams of ammonium dimolybdate was dissolved in 90 ml hot water and then added to the first solution. A very thick white precipitate formed rapidly.

The reaction mixture was refluxed for 1 hour, cooled to room temperature, and filtered as in Example 41. A white solid was recovered and washed four times with water. The solid was vacuum dried for about 2.25 hours at 120° C. The final product was a hydrated white solid weighing 57.84 grams.

EXAMPLE 49

Synthesis of Piperazine Molybdate in Aqueous Solution

Piperazine molybdate having a 2/1 molybdenum/-piperazine molar ratio was prepared as follows. 22.55 grams of piperazine hydrate was dissolved in 50 ml water heated near reflux temperature. 39.09 grams of commercial, so-called "molybdic acid" (actually at least one ammonium molybdate) was dissolved in 275 ml water heated to reflux temperature. The first solution was added to the second solution. A voluminous white precipitate formed rapidly.

The reaction mixture was refluxed for 1.5 hours and filtered hot as in Example 1. A white solid was recovered and washed three times with water and three times with ethanol. The solid was vacuum dried for about 16 hours at 73° C. The final product was 11.77 grams of a low density white powder. It appeared to be photochromic, turning pink after brief exposure to light.

EXAMPLE 50

Synthesis of Piperazine Molybdate in Aqueous HCl Solution

Piperazine molybdate having a 2/1 molybdenum/-piperazine molar ratio was prepared in the presence of HCl as follows. 22.55 grams of piperazine hydrate, 22.86 grams of a 37 wt.% aqueous HCl solution, and 100 ml water were dissolved together and heated to reflux in a 500 ml round-bottomed flask equipped with a stirrer and water-cooled condenser. 39.46 grams ammonium dimolybdate was dissolved in 85 ml hot water and then added to the first solution. A thick precipitate formed rapidly.

The reaction mixture was refluxed for 20 minutes, cooled to room temperature, and filtered as in Example 41. A white solid was vacuum dried for 6 hours at 120° C. The final product was a white solid weighing 36.10 grams. It appeared to be photochromic, turning pink after brief exposure to light.

EXAMPLE 51

Synthesis of Hexamethylenetetramine Molybdate in Aqueous Solution

Hexamethylenetetramine molybdate having a 2/1 molybdenum/hexamethylenetetramine molar ratio was prepared as follows. 10 grams of hexamethylenetetramine was dissolved in 100 ml water heated near reflux temperature. 24.01 grams of commercial, so-called "molybdic acid" (actually at least one ammonium molybdate) was dissolved in 169 ml water heated to reflux temperature. The first solution was added to the second solution.

The reaction mixture was refluxed for about 19 hours, cooled to room temperature, and filtered as in Example 41. A white solid was recovered and washed with water and ethanol. The solid was vacuum dried for about 3 hours at 73° C. The final product was a slightly off-white powder weighing 14.23 grams.

EXAMPLE 52

Synthesis of Hexamethylenetetramine Molybdate in Aqueous HCl Solution

Hexamethylenetetramine molybdate having a 2/1 molybdenum/hexamethylenetetramine molar ratio was prepared in the presence of HCl as follows. 10 grams of hexamethylenetetramine, 14.05 grams of a 37 wt.% aqueous HCl solution, and 100 ml water were dissolved together and heated to reflux in a 500 ml round-bottomed flask equipped with a stirrer and water-cooled condenser. 24.24 grams ammonium dimolybdate was dissolved in 50 ml hot water. The second solution was added to the first solution, and a thin white precipitate formed rapidly.

The reaction mixture was refluxed for 1 hour, cooled to room temperature, and filtered as in Example 41. A white solid was recovered and washed four times with water. The solid weighed 27.50 grams after being vacuum dried for 2 hours at 120° C.

EXAMPLE 53

Synthesis of N,N',N''-Hexaethylmelamine Molybdate in Aqueous HCl Medium

N,N',N''-hexaethylmelamine molybdate having a 2/1 molybdenum/N,N',N''-hexaethylmelamine molar ratio was prepared in the presence of HCl as follows. 10 grams N,N',N''-hexaethylmelamine, 6.69 grams of a 37 wt.% aqueous HCl solution, and 250 ml water were mixed together and heated to reflux in a 500 ml round-bottomed flask equipped with a stirrer and water-cooled condenser. 11.54 grams of ammonium dimolybdate was dissolved in 25 ml hot water and then added to the refluxing mixture. A bright yellow precipitate formed immediately.

The reaction mixture was refluxed for 20 minutes, cooled to room temperature, and filtered as in Example 41. A bright yellow solid was recovered and washed three times with water. The solid weighed 19.32 grams after being vacuum dried for 2.25 hours at 120° C.

EXAMPLE 54

Synthesis of 2-Anilino-4-(2',4'-dimethylanilino)-6-piperidino-1,3,5-triazine Molybdate in Aqueous HCl Medium 2-Anilino-4-(2',4'-dimethylanilino)-6-piperidino-1,3,5-triazine is a substituted melamine having the formula

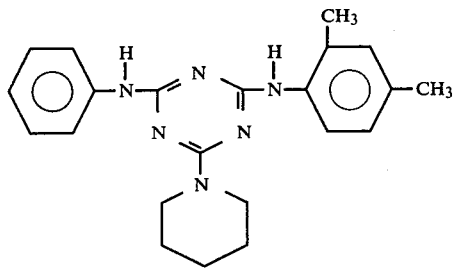

2-Anilino-4-(2',4'-dimethylanilino)-6-piperidino-1,3,5-triazine molybdate having a 2/1 molar ratio of molybdenum to substituted melamine was prepared in the presence of HCl as follows. 5 grams of the substituted melamine, 2.63 grams of a 37 wt.% aqueous HCl solution, 125 ml water and 160 ml ethanol were dissolved together by refluxing in a 500 ml round-bottomed flask equipped with a stirrer and water-cooled condenser. 4.54 grams of ammonium dimolybdate was dissolved in 10 ml hot water and then added to the first solution. An off-white precipitate formed immediately.

The reaction mixture was refluxed for 20 minutes, cooled to room temperature and filtered as in Example 41. An off-white solid was recovered and washed twice with a 50/50 by volume ethanol/water solution and twice with water. The solid weighed 8.22 grams after being vacuum dried for 2.5 hours at 120° C.

EXAMPLE 55

Synthesis of 2,4,6-Tri(N-methylanilino)-1,3,5-triazine Molybdate in Aqueous HCl Medium 2,4,6-Tri(N-methylanilino)-1,3,5-triazine is a substituted melamine having the formula

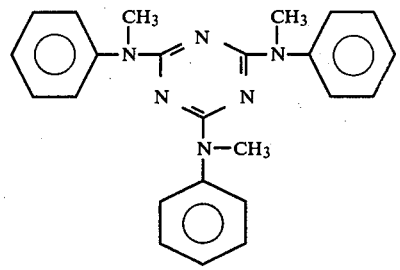

2,4,6-Tri(N-methylanilino)-1,3,5-triazine molybdate having a 2/1 molar ratio of molybdenum to substituted melamine was prepared in the presence of HCl as follows. 7 grams of substituted melamine, 3.48 grams of a 37 wt.% aqueous HCl solution, 75 ml water and 100 ml ethanol were dissolved together by refluxing in a 500 ml round-bottomed flask equipped with a stirrer and water-cooled condenser. 6 grams of ammonium dimolybdate was dissolved in 12 ml hot water and then added to the first solution. A yellow precipitate formed immediately.

The reaction mixture was refluxed for 1.25 hours, cooled to room temperature and filtered as in Example 41. A yellow solid was recovered and washed twice with a 50/50 by volume ethanol/water solution and twice with water. The solid weighed 11.90 grams after being vacuum dried for 4.25 hours at 120° C.

EXAMPLE 56

Synthesis of 2,4,6-tri(morpholino)-1,3,5-triazine Molybdate in Aqueous HCl Medium 2,4,6-Tri(morpholino)-1,3,5-triazine is a substituted melamine having the formula

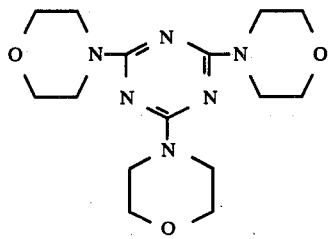

2,4,6-Tri(morpholino)-1,3,5-triazine molybdate having a 2/1 molar ratio of molybdenum to substituted melamine was prepared in the presence of HCl as follows. 3.50 grams of substituted melamine, 2.05 grams of a 37 wt.% aqueous HCl solution, 88 ml water and 88 ml ethanol were dissolved together by refluxing in a 500 ml round-bottomed flask equipped with a stirrer and water-cooled condenser. 3.50 grams of ammonium dimolybdate was dissolved in 8 ml hot water and then added to the first solution. A bright yellow precipitate formed immediately.

The reaction mixture was refluxed for 1 hour, cooled to room temperature and filtered as in Example 41. A yellow solid was recovered and washed twice with a 50/50 by volume ethanol/water solution and twice with water. The solid weighed 6.20 grams after being vacuum dried for 2.5 hours at 120° C.

EXAMPLE 57

Synthesis of 2,2,4-Trimethyl decahydroquinoline Molybdate in Aqueous HCl Solution 2,2,4-Trimethyl decahydroquinoline molybdate having a 2/1 molybdenum/2,2,4-trimethyl decahydroquinoline molar ratio was prepared as follows. 10 grams 2,2,4-trimethyl decahydroquinoline, 16.30 grams of a 37 wt.% aqueous HCl solution and 250 ml water were dissolved together and heated to reflux in a 500 ml round-bottomed flask equipped with a stirrer and water-cooled condenser. 28.12 grams ammonium dimolybdate was dissolved in 50 ml hot water. The second solution was added to the first solution. A yellow precipitate formed immediately.

The reaction mixture was refluxed for 15 minutes, cooled to room temperature, and filtered as in Example 41. A yellow solid was recovered and washed three times with water. A fluffy yellow solid weighing 29.97 grams was produced after being vacuum dried for 2.25 hours at 70° C.

EXAMPLES 58-61

Examples 58-61 demonstrate the superior smoke retarding properties of melamine molybdate in the NBS Smoke Chamber Test. Substantially smaller levels of molybdenum were present in the melamine molybdate than in $MoO_3$, yet melamine molybdate exhibited better smoke retarding effects in both 5 and 10 wt. part comparisons. Moreover, melamine molybdate was white and dispersed readily in polyvinyl chloride to give white or slightly off-white compositions. In contrast, $MoO_3$ was colored and produced a significantly discolored, bluish-gray composition when mixed with polyvinyl chloride.

The following recipe was used:

| MATERIAL | WT. PARTS |
| --- | --- |
| Polyvinyl Chloride+ | 100 |
| Melamine Molybdate++ | Variable |
| Polyethylene Powder | 2 |
| Dibutyl Tin Bis Isooctyl Thioglycollate | 2 |

+Homopolymer having an inherent viscosity of about 0.98–1.04; ASTM Classification GP-5-15443.
++The control sample contained no melamine molybdate.

Each experimental sample was prepared by milling the recipe materials on a two-roll mill for about 5 minutes at a roll surface temperature of about 320° F. The milled samples were pressed into 6×6×0.025 inch sheets. Pressing was done at about 320°–330° F. using 40,000 lbs. of force applied to a 4-in. ram. The samples were given a 3–5 minute preheat prior to pressing for 8 minutes under full load.

The molded samples were cut into $2\frac{7}{8} \times 2\frac{7}{8} \times 0.025$ inch sections. Testing was performed using the flaming mode of the NBS Smoke Chamber Test (ASTM STP 422, pp. 166–204) described heretofore. Test results are given in Table III.

TABLE III

| | | Additive | | | | |
| --- | --- | --- | --- | --- | --- | --- |
| Example | Compound | Molybdenum/ Amine Molar Ratio | Additive Amount (phr) | Molybdenum Content (phr) | Maximum Smoke Density per Gram of Sample ($D_m/g$) | Smoke Reduction (%) |
| Control | None | — | — | — | 74.42 | — |
| 58 | Melamine Molybdate | 2 | 5 | 2.3 | 24.27 | 67 |
| 59 | $MoO_3$ | — | 5 | 3.3 | 30.00 | 60 |
| 60 | Melamine Molybdate | 2 | 10 | 4.5 | 23.05 | 69 |
| 61 | $MoO_3$ | — | 10 | 6.7 | 26.08 | 65 |

EXAMPLES 62-65

Examples 62–65 demonstrate the superior smoke retarding effects of melamine molybdate in the Goodrich Smoke-Char test. Substantially smaller levels of molybdenum were present in the melamine molybdate than in $MoO_3$, yet melamine molybdate exhibited better smoke retarding effects in both 5 and 10 wt. part comparisons. Moreover, melamine molybdate was white and dispersed readily in polyvinyl chloride to give white or slightly off-white compositions. In contrast, $MoO_3$ was colored and produced a significantly discolored, bluish-gray composition when mixed with polyvinyl chloride.

The same recipe was used as in Examples 58–61. Milling and molding procedures were also the same. The molded samples were cut into small (about 0.3 gram) samples for testing. Test results are set forth in Table IV.

TABLE IV

| Example | ADDITIVE Compound | Molybdenum/Amine Molar Ratio | Additive Amount (phr) | Molybdenum Content (phr) | Smoke Formation Per Gram of sample | Smoke Reduction (%) |
|---|---|---|---|---|---|---|
| Control | None | — | — | — | 90.7 | — |
| 62 | Melamine Molybdate | 2 | 5 | 2.3 | 41.1 | 55 |
| 63 | MoO$_3$ | — | 5 | 3.3 | 66.9 | 26 |
| 64 | Melamine Molybdate | 2 | 10 | 4.5 | 23.3 | 74 |
| 65 | MoO$_3$ | — | 10 | 6.7 | 27.4 | 70 |

EXAMPLES 66–78

Examples 66–78 demonstrate the utility of amine molybdates as smoke retardants in polyvinyl chloride compositions. The NBS Smoke Chamber Test was used, with recipe, sample preparation and testing procedure being the same as for Examples 58–61. Test results are presented in Tables V and VI.

TABLE V

| Example | Additive Compound | Molybdenum/Amine Molar Ratio | Additive Amount (phr) | Molybdenum Content (phr) | Maximum Smoke Density Per Gram Of Sample (D$_m$/g) | Smoke Reduction (%) |
|---|---|---|---|---|---|---|
| Control | — | — | — | — | 52.87 | — |
| 66 | Ethylamine Molybdate | 1 | 5 | 2.54 | 34.11 | 35 |
| 67 | Pyridine Molybdate | 2 | 5 | 2.35 | 32.49 | 39 |
| 68 | Piperazine Molybdate | 2 | 5 | 2.57 | 24.77 | 53 |
| 69 | Hexamethylenetetramine Molybdate | 2 | 5 | 2.24 | 38.34 | 27 |

TABLE VI

| Example | Additive Compound | Molybdenum/Amine Molar Ratio | Additive Amount (phr) | Molybdenum Content (phr) | Maximum Smoke Density Per Gram Of Sample (D$_m$/g) | Smoke Reduction (%) |
|---|---|---|---|---|---|---|
| Control | — | — | — | — | 54.78 | — |
| 70 | Ethylenediamine Molybdate | 2 | 5 | 2.76 | 29.46 | 46 |
| 71 | Guanidine Molybdate | 2 | 5 | 2.36 | 29.98 | 45 |
| 72 | Aniline Molybdate | 2 | 5 | 2.52 | 26.16 | 52 |
| 73 | N,N-dimethylaniline Molybdate | 2 | 5 | 2.35 | 24.83 | 55 |
| 74 | N,N',N''-Hexaethyl-melamine Molybdate | 2 | 5 | 1.65 | 22.38 | 59 |
| 75 | 2-Anilino-4(2',4'-dimethylanilino)-6-piperidino-1,3,5-triazine Molybdate | 2 | 5 | 1.45 | 29.85 | 46 |
| 76 | 2,4,6-Tri(N-methylanilino)-1,3,5-Triazine Molybdate | 2 | 5 | 1.40 | 30.85 | 44 |
| 77 | 2,4,6-Tri(morpholino)-1,3,5-Triazine Molybdate | 2 | 5 | 1.54 | 26.48 | 52 |
| 78 | 2,2,4-Trimethyl decahydroquinoline Molybdate | 2 | 5 | 2.04 | 30.01 | 45 |

The improved smoke retardant vinyl chloride and vinylidene chloride polymer compositions of this invention are useful wherever smoke resistance is desirable, such as in carpets, house siding, plastic components for airplane interiors, and the like. Of course, overall suitability for a particular use will depend upon other factors as well, such as comonomer type and level, compounding ingredient type and level, polymer particle size, and the like.

I claim:

1. A heterocyclic amine molybdate wherein the heterocyclic amine used in producing the molybdate is melamine or a substituted melamine having the formula

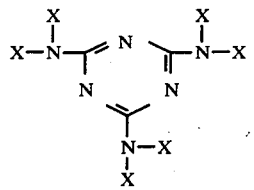

X being hydrogen or an alkyl, alicyclic, aralkyl, alkaryl or aryl group containing from 1 to 10 carbon atoms.

2. A composition of claim 1, melamine molybdate.

3. A composition of claim 1, N,N',N''-hexaethylmelamine molybdate.

4. 2-Anilino-4-(2',4'-dimethylanilino)-6-piperidino-1,3,5-triazine molybdate.

5. A composition of claim 1, 2,4,6-tri(N-methylanilino)-1,3,5-triazine molybdate.

* * * * *